US00PP12134P2

(12) United States Plant Patent
Deroose

(10) Patent No.: US PP12,134 P2
(45) Date of Patent: Oct. 9, 2001

(54) GUZMANIA PLANT NAMED 'CELINA'

(75) Inventor: Reginald Deroose, Evergem (BE)

(73) Assignee: Deroose Plants BVBA, Evergem (BE)

( * ) Notice: Subject to any disclaimer, the term of this patent is extended or adjusted under 35 U.S.C. 154(b) by 0 days.

(21) Appl. No.: 09/419,917

(22) Filed: Oct. 18, 1999

(51) Int. Cl.[7] ..... A01H 5/00
(52) U.S. Cl. ..... Plt./371
(58) Field of Search ..... Plt./371

(56) References Cited

U.S. PATENT DOCUMENTS

P.P. 9,476 * 3/1996 Kent ..... Plt./371
P.P. 10,069 * 10/1997 Kent ..... Plt./371
P.P. 10,383 * 5/1998 Box ..... Plt./371

OTHER PUBLICATIONS

GTITM UPOVROM Citation for 'Celina' as per QZ PBR 991029; Jul. 19, 1999.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A Guzmania plant named 'Celina' characterized by having vigorous plant with long arching leaves; variegated foliage with a reddish-pink and cream-white linear band and a few green striations; and inflorescence with red scape bracts and yellow and red floral bracts which is slightly compressed where the primary bracts are positioned.

1 Drawing Sheet

BACKGROUND OF THE INVENTION

The present invention comprises a new and distinct cultivar of Guzmania plant, hereinafter referred to by the cultivar name 'Celina'. The genus Guzmania is a member of the family Bromeliaceae.

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Desirably, the plants are shaded from direct sunlight, and during the spring to autumn period, the central vase-like part of the leaf rosette is desirably filled with water.

Guzmania is native to tropical America. Leaves of Guzmania are usually formed as basal rosettes, which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots produced by the plant which may then be rooted. The resulting plantlets are detached from the mother plant and may be potted in a suitable growing mixture.

The new cultivar was discovered as a naturally occurring mutation among plants of the parent cultivar 'Gisela G24' (unpatented), which is a non-variegated Guzmania plant. The female parent of 'Gisela G24' was Guzmania 'Magnifica' (unpatented). The male parent of 'Gisela G24' was an unnamed and unpatented plant of *Guzmania zahnii*. 'Celina' was discovered and selected among plants of the cultivar 'Gisela G24' by the inventor, Reginald Deroose, in 1987 in a controlled environment in Evergem, Belgium.

'Celina' is characterized by its medium to large plant size and its variegation on the leaves that is a linear band of reddish-pink at the sheath becoming creamy white at one-third of the leaf. The inflorescence is red with yellow and the part where the primary bracts are positioned is slightly compressed.

The first act of asexual reproduction of the new cultivar was performed by the inventor in 1987, from offshoots produced by the plant. Horticultural examination of these asexually reproduced plants initiated in 1987 has demonstrated that the combination of characteristics as herein disclosed for 'Celina' are firmly fixed and retained through successive generations of asexual reproduction.

BRIEF DESCRIPTION OF THE INVENTION

The following traits have been repeatedly observed and are determined to be basic characteristics of 'Celina' which in combination distinguish this Guzmania as a new and distinct cultivar:

1. Vigorous plant with long arching leaves;

2. Variegated foliage with a reddish-pink and cream-white linear band and a few green striations; and 3. Inflorescence with red scape bracts and yellow and red floral bracts and slightly compressed where the primary bracts are positioned.

'Celina' has not been observed under all possible environmental conditions. The phenotype of the new cultivar may vary significantly when grown under different conditions of temperature, light and other determining factors without any change in genotype.

Of the many commercial cultivars known to the present inventor, the most similar in comparison to 'Celina' is the parental cultivar Guzmania 'Gisela G24'. The inflorescence and plant shape of 'Celina' are similar to the inflorescence and plant shape of 'Gisela G24'. However, the leaves of 'Celina' are strongly variegated whereas 'Gisela G24' has entirely green leaves. The leaves of 'Celina' are also more arching whereas 'Giseala G24' has more erect leaves.

BRIEF DESCRIPTION OF THE DRAWING

The accompanying photographic illustration shows a perspective view of the foliage and inflorescence characteristics of a typical 'Celina' plant following growth under appropriate growing conditions, with colors being as true as possible with illustrations of this type.

DETAILED BOTANICAL DESCRIPTION

The following observations, measurements and values describe plants grown in Evergem, Belgium, under greenhouse conditions which closely approximate those generally used in horticultural practice. The plant described is approximately 13 months old from a 25 cm long cutting, for a plant height of 50 cm. Color references are made to The Royal Horticultural Society Colour Chart (R.H.S.), except where general colors of ordinary significance are used.

Classification:

*Commercial.*—Guzmania c.v. 'Celina'.

*Species.*—Guzmania 'Celina' is a variegated mutation of Guzmania 'Gisela G24'; Guzmania 'Gisela G24' is Guzmania 'Magnifica' (cultivar of lingulata v. cardinalis×lingulata minor)×*Guzmania zahnii.*

Parentage: Naturally occurring mutation of Guzmania 'Gisela G24'.

Propagation: Vegetative, by removal of offsets.

Plant:

*Form.*—Funnel-form rosette.

*Height.*—Approximately 45–50 cm when in full bloom.

*Diameter.*—Approximately 90–95 cm.

*Growth habit.*—Vigorous, it takes approximately 13 months to produce a finished flowering plant from a 25 cm long cutting, in a standard heated greenhouse with temperatures during the day of 20 degrees Celsius, and 18 degrees Celsius at night.

Foliage:

*Habit.*—Arcuate spreading, standing up at an angle of 45° and bending downwards from the middle.

*Size.*—Approximately 45–55 cm long.

*Leaf sheaths.*—Elliptic, 7 cm wide; glabrous surface; margins are entire and green (RHS 147A), striations and suffused with red (RHS 59A); center is reddish-pink (RHS 58A to 63C) with a few irregularly green striations (RHS 147A); (all color designations are for both upper and lower surfaces).

*Leaf blades.*—Ligulate, glabrous surface; apex is acute to attenuate, 2.0–3.5 cm wide, variegated from one-half to two-thirds of the leaf surface. Margins are entire and green (RHS 147A) with cream to yellow-green center (RHS 160B) with a few irregularly green striations (RHS 147A). The leaves on the scape have a pinker center (approximately RHS 58D); (all color designations are for both upper and lower surfaces).

*Scape.*—Round, approximately 45–50 cm long and 1 cm in diameter.

*Scape bracts.*—10, acute to attenuate apex, margin entire, glabrous surface, imbricate, foliaceous, concealing the scape, arcuate spreading, 5–10 cm long and 2–3 cm wide, variegation similar to the leaves. Scape bracts gradually become primary bracts from the bottom to the top with appearance of red coloring of the bracts, reddish-pink (color varying between RHS 48A and RHS 48B) to red (RHS 46B) (Color designations represent both upper and lower surfaces).

*Number of leaves.*—Approximately 30 to 40.

Inflorescence:

*Habit.*—Spike, round, approximately 10–12 cm in diameter, the part where the primary bracts are positioned is slightly compressed with approximately 12 spirally arranged bracts that end at an angle of 45° to 90°.

*Primary bracts.*—20, elliptic shape, margin is entire, sessile base, apex is acute to attenuate, 5–6 cm long and 1.5–2.0 cm wide; red (RHS 46B) (Both surfaces).

*Floral bracts.*—1 floral bract per flower, elliptic shape, cucullate apex, sessile base, margin is entire, approximately 1 cm wide, floral bracts are closely folded around the flowers, 3.5 cm long and 1.5–2.0 cm wide; top is yellow (RHS 7A) and the base is red (RHS 34A); (all colors are for both upper and lower surfaces).

*Flowers.*—Diameter: 5 mm. Length: 1.5–2 cm. Sepals: 3, yellow (RHS 6A) (Both surfaces); elliptic shape; approximtely 1.2–2 cm long; 5 cm wide; sessile base; margin is entire; acute apex. Petals: 3, yellow (RHS 15C) (Both surfaces); shape is elliptic; approximately 0.8–1.2 cm long, 3–5 mm wide, obtuse apex, margin entire, partially fused at the base. Stamens: 6 per flower, approximately 1.8 cm long, 1 style with 3 lobed stigma per flower, lower parts of filaments fused with corolla. Pistils: 3 per flower, approximately 2.5 cm long.

*Duration of flowers.*—Individual flowers last for one day and the total duration of flowering is approximately 12 weeks.

*Buds.*—Elliptic shape, approximately 1.5–2 cm long, 4–5 mm diameter, yellow (RHS 15C).

Other significant characteristics: The inflorescence holds its color for approximately 5–7 months.

Pollen: No known pollen produced.

Fruit: No fruit produced.

Disease/pest resistance/susceptibility: No specific resistance or susceptibility observed.

I claim:

1. A new and distinct Guzmania plant named 'Celina' substantially as illustrated and described herein.

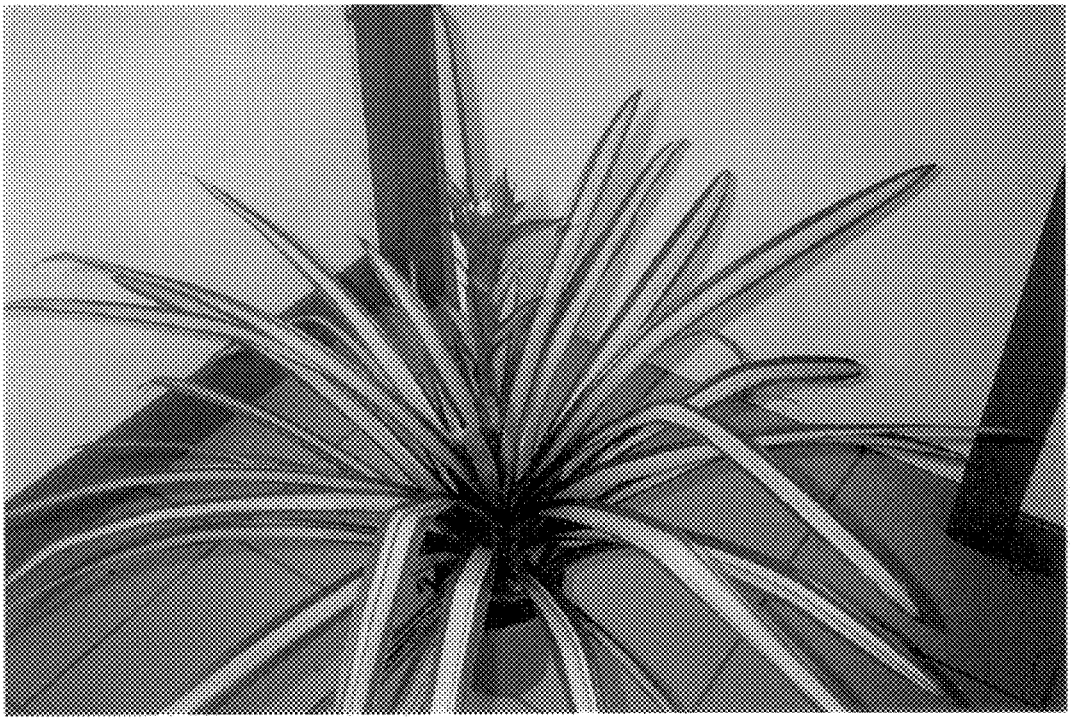

* * * * *